United States Patent [19]
Lavie et al.

[11] Patent Number: 6,056,961
[45] Date of Patent: May 2, 2000

[54] PLANT EXTRACTS FOR THE PREPARATION OF PHARMACEUTICAL COMPOSITIONS FOR THE TREATMENT OF HEPATITIS

[76] Inventors: David Lavie, 6 Ruppin Street, Rehovot, Israel, 76353; Anne Steinbeck-Klose, 24 Aloise Schulte Strasse, Bonn, Germany

[21] Appl. No.: 08/990,340

[22] Filed: Dec. 15, 1997

[30] Foreign Application Priority Data

Dec. 15, 1996 [IS] Iceland ..................................... 119833

[51] Int. Cl.⁷ ........................... A61K 31/05; A61K 31/12
[52] U.S. Cl. .................................... 424/195.1; 435/235.1; 514/732; 514/738
[58] Field of Search ...................... 424/195.1; 435/235.1; 514/732, 738

[56] References Cited

U.S. PATENT DOCUMENTS

| | | | |
|---|---|---|---|
| 4,704,281 | 11/1987 | Elthes et al. | .......................... 424/195.1 |
| 4,898,891 | 2/1990 | Lavie et al. | . |
| 5,834,443 | 11/1998 | Masiello | .................................... 514/44 |

FOREIGN PATENT DOCUMENTS

| | | |
|---|---|---|
| 0256452 | 2/1988 | European Pat. Off. . |
| 79661 | 8/1986 | Israel . |
| WO 89/01329 | 2/1989 | WIPO . |

OTHER PUBLICATIONS

S. Chris Pappas, Jay H. Hoofnagle, Neal Young, Stephen E. Straus, and E. Anthony Jones, Treatment of Chronic Non–A, Non–B Hepatitis With Acyclovir: Pilot Study, Journal of Medical Virology 15:1–9 (1985).

Edward Tabor, Kenichi Kobayashi, Hepatitis C Virus, a Causative Infectious Agent of Non–A, Non–B Hepatitis: Prevalance and Structure—Summary of a Conference on Hepatitis C Virus as a Cause of Hepatocellular Carcinoma, Journal of the National Cancer Institute vol. 84:86–90 (1992).

Qui–Lim Choo, George Kuo, Amy J. Weiner, lacy R. Overby, Daniel W. Bradley, Michael Houghton, Isolation of a cDNA Clone Derived from a Blood–Borne Non–A, Non–B Viral Hepatitis Genome, Science, vol. 244:359–362 (1989).

Saez–Royuela, F, JC Porres, A Moreno, I Castillo, G Martinez, F Gallana and V Carreno. 1991, High Doses of Recombinant Alfa–Interferon or Gamma–Interferon for Chronic Hepatitis C: A Randomized Controlled Hepatology 13: 327–331.

Dusheiko G and P, Simmons 1994. Sequence Variability of Hepatitis C Virus and its Clinical Significance (Review, J. Viral Hepatitis 1: 3–15.

Kanai K, M Kato and H Okamoto 1992, HCV genotypes in chronic hepatitis C and response to interferon, Lancet 339: 1543.

Yoshioka K, S Kakumu, T Wakita et al. 1992, Detection of hepatitis C virus by polymerase chain reaction and response to IFN–a therapy: relationship to genotypes of hepatitis C virus, Hepatology 16: 293–299.

Kakumu S., Yoshioka K., Wakita T., Ishikawa T., Takayanagi M, and Higashi Y. A pilot study of Ribavirin and interferon beta for the treatment of chronic hepatitis C. Gastroenterology 1993, 105: 507–512.

Moraleda G, TT Wu, AR Jilbert, CE Aldrich, LD Condreay. SH Larsen, JC Tang, M Colacino, WS Mason, 1993: Inhibition of duck hepatitis B virus replication by hypericin. Antiviral Res. 20: 235–247.

Lavie, G, F. Valentine, B. Levin, Y. Mazur, G. Gallo, D. Lavie, D. Weiner, D. Meruelo, 1989: studies of the mechanisms of action of the antiretroviral agents hypericin and pseudohypericin. Proc. Natl. Acad. Sci. (USA) 86: 5963–5967.

"Hypericin Vimrxyn", Drugs of the Future, vol. 21, No. 5, 1996, pp. 555–556.

Gloria Moraleda, et al., "Inhibition of Duck Hepatitis B Virus Replication by Hypericin", Antiviral Research, vol. 20, No. 3, Mar. 1993, pp. 235–247.

Tyler. *Herbs of Choice*. 1994. pp. 122–124, 1994.

Kinghorn et al. *Human Medicinal Agents from Plants*, p. 32, 1993.

*Primary Examiner*—Leon B. Lankford, Jr.
*Attorney, Agent, or Firm*—Amster, Rothstein & Ebenstein

[57] ABSTRACT

The use of extracts from the plant *Hypericum perforatum* in the preparation of pharmaceutical compositions for the treatment of hepatitis C, chronic hepatitis C and related viruses, said pharmaceutical compositions comprising at least one extract of the plant *Hypericum perforatum* and optionally in addition, one or more pharmaceutically acceptable inactive components, selected from, carriers, coatings, diluents and adjuvants.

11 Claims, 2 Drawing Sheets

PLANT EXTRACTS FOR THE PREPARATION OF PHARMACEUTICAL COMPOSITIONS FOR THE TREATMENT OF HEPATITIS

FIELD AND BACKGROUND OF THE INVENTION

The present invention involves the use of extracts of the plant *Hypericum perforatum* in the preparation of improved pharmaceutical compositions for the treatment, prevention and control of hepatitis C, chronic hepatitis and related viruses.

Hepatitis C is a debilitating liver disease that begins as an acute infection and can develop into a chronic disease. As many of 50% of acutely infected individuals develop a state of chronic infection [Alter H J 1988. Transfusions-associated non-A, non-B hepatitis: the first decade In Viral Hepatitis and Liver Disease. Zuckerman A. J. ed. Alan R. Liss, New York, p. 537–542] of which up to 20% may proceed to hepatic cirrhosis (destruction of the liver) with its complications of portal hypertension, ascites, encephalopathy, and bleeding disorders. The infection also poses a high risk for development of liver cancer (hepatocellular carcinoma). The prevalence of infection in the general population is so high that prior to the availability of screening tests, the risk of hepatitis C following blood transfusion in the United States was 5–10% or about 150,000–300,000 transfusion recipients per year acquired the disease. In Japan 4% of screened blood donors over age 55 had serologic evidence of HCV infection [Tabor E. and K. Kabayashi 1992. Hepatitis C virus, a causative infectious agent for non-A, non-B hepatitis: Prevalence and structure—Summary of a conference on hepatitis C virus as a causative of hepatocellular carcinoma: J. Natl. Cancer Inst. 84:86–90] In some endemic regions of the Third World as many as 20% of the population can be infected. The healthy appearance of some chronic carriers may change after contraction of other illnesses that can reduce their immunity. The carriers can transmit the hepatitis C virus to others with whom they have close contact, thereby spreading the disease.

Hepatitis C is caused by a virus known as hepatitis C virus (HCV). HCV is non-integrating, lipid-enveloped positive sense RNA virus, similar to flavivirus and pestiviruses in gene organization and in mechanisms of cell invasion, with a single open reading frame [Choo Q L, G Kuo, A J Weiner, L R Overby, D W Bradley and M Houghton 1989. Isolation of a cDNA clone derived from a blood-borne non-A, non-B viral hepatitis genome. Science 244:359–362, Tabor/Kabayashi 1992]. The virus is transmitted by the parenteral route in the case of transfusion and drug abuse; and by uncertain mechanisms that probably include a sexual mode of transmission in other cases.

Treatment of chronic hepatitis C

A search for effective means of treating chronic hepatitis C is essential due to the high prevalence of hepatitis C, its major morbidity for symptomatic patients, the insidiously progressive course, the infectious potential of carriers, and the long-term risk for development of hepatocellular carcinoma. The primary goals of therapy should be to reduce the release of liver enzymes into the blood circulation bringing about a biologic and histologic improvement of disease activity, and secondary objectives should be to decrease viral replication and viral load with the ultimate goal of complete elimination of the virus. Virus load emerges as the most reliable means of evaluating treatment response. Techniques to characterize and quantify hepatitis C infection continue to evolve. Newly developed assays utilizing branched DNA technology (bDNA) (Chiron Ltd.), and Roche's HCV-RNA RT-PCR assay may permit simple quantification of viral RNA levels in serum. The clinical significance of these assays is beginning to be established in larger, multicenter, prospective studies.

Despite its high prevalence and moribund clinical course, there is no established form of effective therapy for hepatitis C infections. Acyclovir treatments were unsatisfactory [Pappas S C, J H Hoofnagle, N Young, S E Straus, and E A Jones, 1985. Treatment of chronic non-A, non-B hepatitis with acyclovir: A pilot study. J. Med. Virol 15:1–9], and IFN-gamma, despite its known antiviral activity, has also proven ineffective (Saez-Royuela F, J C Porres, A Moreno, I Castillo, G Martinez, F Gallana and V Carreno. 1991. High doses of recombinant alfa-interferon or gamma-interferon for chronic hepatitis C: A randomized controlled trial Hepatology 13:327–331). The best results to date have been obtained with IFN-a, although relief was temporary, long-term response rates have been disappointing and generally run between 15–25% (Dusheiko G and P. Simmons 1994. Sequence variability of hepatitis C virus and its clinical significance (Review). J Viral Hepatitis 1:3–15). The responses were found to be related to the HCV genotype (Kanai K, M Kato and H Okamoto 1992. HCV genotypes in chronic hepatitis C and response to interferon, Lancet 339:1543, Takada N, S Takase, N Enomoto, A Takada and T Date. 1992. Clinical backgrounds of the patients having different types of hepatitis C virus genomes. J Hepatol. 14:35–40, and Yoshioka K, S Kakumu, T Wakita et al. 1992, detection of hepatitis C virus by polymerase chain reaction and response to IFN-a therapy: relationship to genotypes of hepatitis C virus. Hepatology 16:293–299), to HCV titres and to the duration of disease. A long duration of disease is an adverse prognostic factor and a prediction of therapy failure. Thus, the time factor for interferon therapy is crucial and therapy, should begin early to succeed. Most recently interferon-β treatments have been given in combination with ribavirin. The results were not encouraging as sustained responses occurred in only one third of the patients (Kakumu S., Yoshioka K., Wakita T., Ishikawa T., Takayanagi M, and Higashi Y. A pilot study of Ribavirin and interferon beta for the treatment of chronic hepatitis C. Gastroenterology 1993, 105:507–512). This form of treatment has been associated with quite severe side effects and could be given for limited time intervals.

The present invention predicted and discovered that treatment of patients with chronic active hepatitis C with preparations from *Hypericum perforatum* led to dramatic declines in HCV blood levels in these patients. In some cases the patients tested negative to HCV in extremely sensitive molecular assays such as the quantitative RT-PCR for hepatitis C virus or the branched DNA technology, inferring that no virus particles could be detected in their blood by these most sensitive and sophisticated detection techniques. The virus appears to have been completely eliminated. The preparations that were used are in most cases dried alcoholic extracts of the aerial parts of the plant *Hypericum perforatum*. They contain, among other compounds also hypericin and pseudohypericin. These are two photodynamic compounds which are activated by light and are known to act as virucidal agents (Moraleda G, T T Wu, A R Jilbert, C E Aldrich, L D Condreay. S H Larsen, J C Tang, M Colacino, W S mason, 1993: Inhibition of duck hepatitis B virus replication by hypericin. Antiviral Res. 20:235–247; Lavie, G, F. Valentine, B. Levin, Y. Mazur, G. Gallo, D. Lavie, D.

Weiner, D. Meruelo. 1989: Studies of the mechanisms of action of the antiretroviral agents hypericin and pseudohypericin. Proc. Natl. Acad. Sci. (USA) 86:5963–5967), however, the inventor has discovered that the plant extracts contain potentiating activity that obviates the need for light and renders the plant extracts with potent antiviral activity against HCV without any need for light which is required with synthetic hypericin or pseudohypericin.

The healing process in this disease appears to be the result of inhibition of hepatitis C virus replication by the hypericum dried preparations. Over time the reservoir of infected cells dies due to the toxic effect of the virus. Prevention of infection of new liver cells or other bloods mononuclear cells by free hepatitis C virus that circulates in the blood that will bring about elimination of the infected state. The liver then has a chance to slowly regenerate and return to normal function.

SUMMARY OF THE INVENTION

The present invention involves the use of extracts of the plant *Hypericum perforatum* in the preparation of pharmaceutical compositions for the treatment of hepatitis C, chronic hepatitis and related viruses, said compositions comprising at least one extract of the plant *Hypericum perforatum* and optionally in addition, one or more pharmaceutically acceptable inactive components selected from, carriers, coatings, diluents and adjuvants.

As non-limiting examples of extractants, one may mention commonly available mono or polyhydric alcohols, acetone and similar ketones either alone in aqueous or non-aqueous combinations. The extraction itself can be carried out at ambient or elevated temperatures, or by other extraction methods commonly used for such purposes. The extraction can also include removal of fatty component impurities, by a pre-extraction with non-polar solvents. Non-limiting examples of such solvents include ethy acetate, petroleum ether or combinations thereof.

The pharmaceutical compositions themselves, can be adapted for convenient administration by known methods and in known forms, e.g., for oral or parenteral administration.

DETAILED DESCRIPTION OF THE INVENTION

Plants of *Hypericum perforatum* are readily available from various sources. To obtain the extracts necessary to prepare the pharmaceutical compositions of the present invention, they are normally harvested, dried and milled to a crude powder form. The powder so obtained is then subjected to extraction with aqueous or non-aqueous monohydric or polyhydric alcohols, acetone and similar solvents. The extracts so obtained may be evaporated to dryness, concentrated or diluted as desired or as required for the preparation of the final pharmaceutical compositions required or desired. The extraction can also include prior removal of fatty component impurities, by a pre-extraction with non-polar solvents. Non-limiting examples of such solvents include ethyl acetate, petroleum ether or combinations thereof.

Alternatively, extracts of *Hypericum perforatum* can be obtained commercially from various convenient sources, and can be used in the preparation of the pharmaceutical compositions of the subject invention.

The said pharmaceutical compositions, provide a convenient and effective means for treatment of chronic hepatitis C virus infections and similar viruses, with clear advantages over other means.

The present invention provides a method for treatment of chronic hepatitis C virus infection that will reduce and eventually eliminate the virus from the infected individual. The treatment that eliminates or reduces the HCV virus load reduces the risk of liver cirrhosis (destruction of the liver), reduces the need for such patients to undergo liver transplantation, and reduces the risk of these patients developing liver cancer (hepatocellular carcinoma).

The treatment comprises administering to a patient pills or capsules of enriched extracts of *Hypericum perforatum* on a daily basis, 2–3 times per day for long periods of time, many months and possibly also numerous years. In some patients the decline in virus load is rapid and in others it requires a few moonths before virus titres decline significantly, tenfold or more in comparison with pretreatment levels. The improvements in liver function notes by decline in the blood levels of liver specific enzymes such as the transaminase SGPT can require many months. The suggested doses of Hypericum therapy will range from 1–50 capsules or tablets of Hypericum of preparations that contained 0.20–0.28% of total hypericin or preferentially 1–20 tablets/capsules of said Hypericum preparations. Preferred therapy will include doses of 1–20 tablets/capsules of *Hypericum perforatum* preparation that contained 0.38–0.50% of total hypericin, and which will be administered orally or parenterally to provide a total daily dose equivalent to 1–10 mg of total hypericin per patient per day.

EXAMPLES

Patients with chronic hepatitis C were first confirmed to have infection with the hepatitis C virus and their virus titres were determined prior to the administration of therapy by quantitative PCR using the kit by Hoffman La Roche, or by the branched DNA technology using the kit by Chiron. The patients were then administered with *Hypericum perforatum* therapy. Dried preparation of extracts of *Hypericum perforatum* calibrated to contain 0.2% or 0.4% of hypericin-pseudohypericin known as total hypericin were used. The ratio between the two reagents was generally ⅔ pseudohypericin and ⅓ hypericin. The doses varied from 4 tablets/capsules of approximately 250 mg each given 3 times a day to a 70–80 kg patient (3×4 capsules/day) of preparations that contained 0.20–0.28% of total hypericin to 2×2 tablets/capsules per day in smaller patients who weighed 55–65 kg with preparations that contained 0.4% total hypericin. The patients were seen as approximately 3 month intervals at which they were requested to perform blood chemistry and hematology analyses that include blood levels of liver enzymes and quantitative analyses of blood virus levels.

Figure 1A:
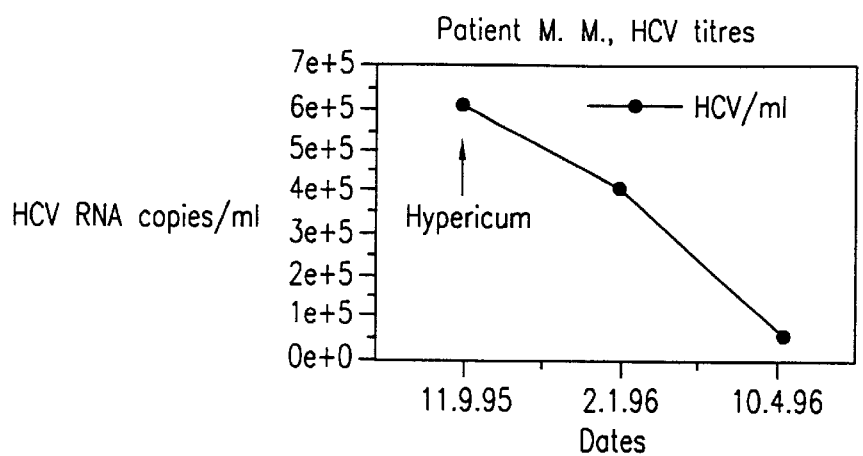
FIGS. 1(*a*–*d*) shows the HCV blood virus load assays at different times before and after patient treatment with *Hypericum perforatum* preparations.
Figure 1B:
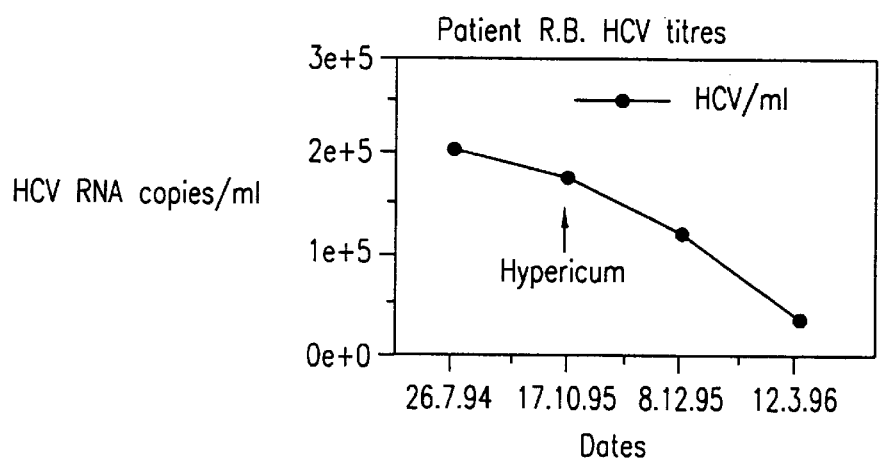
Figure 1C:
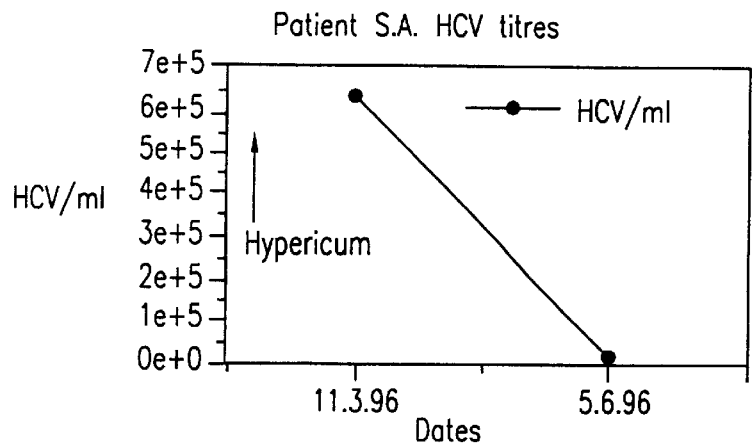
Figure 1D:
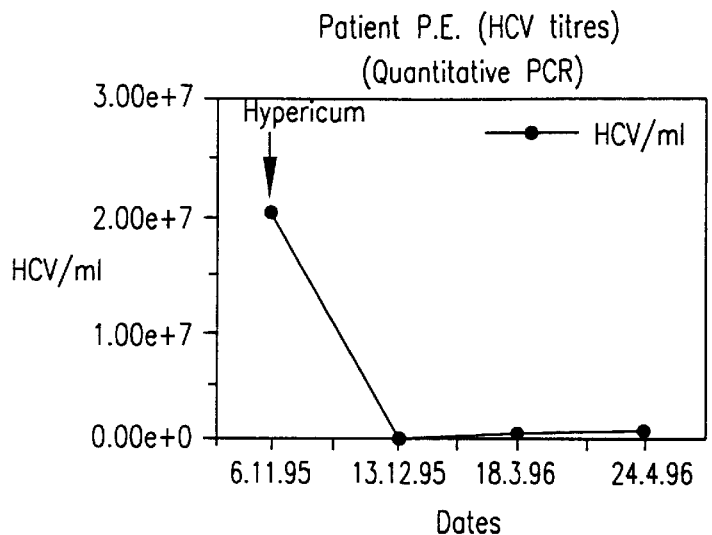
Figure 2A:
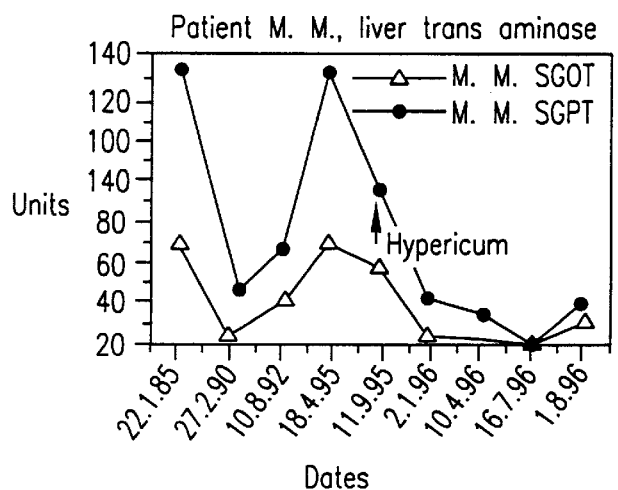
FIGS. 2(*a*–*b*) shows the results of liver enzyme assays for serum glutamic oxaloacetc trans aminase (SGOT) and serum glutamic pyruvic trans aminase (SGPT) assays following patient treatment with *Hypericum perforatum* preparations.
Figure 2B:
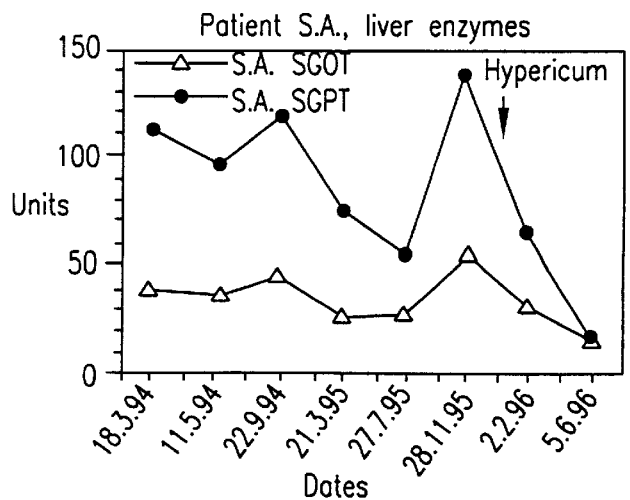

While certain embodiments of the invention have been particularly described, it will be apparent to those skilled in the art that many modifications and variations may be made. The invention is accordingly not to be construed as restricted to such embodiments, rather its concept, scope and spirit are to be understood having regard to the claims which follow:

What is claimed is:

1. A method for treating hepatitis C in a patient infected with the hepatitis C virus, comprising administering to said patient infected with the hepatitis C virus, on a daily basis for a period of at least three months, between about 1 to about 5 grams of an extract from the plant *Hypericum perforatum*, said extract having a total hypericin content between about 0.2% and about 0.4% by weight.

2. A method according to claim 1, wherein said total hypericin comprises pseudohypericin and hypericin in a weight of about 2:1.

3. A method according to claim 1, wherein the total hypericin content contained in said extract administered to said patient is between about 0.0615 mg and about 1.2 mg total hypericin per kilogram of patient body weight per day.

4. A method according to claim 3, wherein said total hypericin comprises pseudohypericin and hypericin in a weight ratio of about 2:1.

5. A method according to claim 1, wherein said extract is administered in an amount of about 3 grams of extract per day.

6. A method according to claim 5, wherein said extract has a total hypericin content of between about 0.20% and 0.28% by weight.

7. A method according to claim 1, wherein said extract is contained in a pharmaceutical composition in unit dosage form.

8. A method according to claim 7, wherein said pharmaceutical composition is selected from the group comprising capsules and tablets.

9. A method according to claim 8, wherein the administration of said extract is effected by administering to said patient from two to four dosage units twice or thrice daily, thereby administering from 4 to 12 dosage units daily.

10. A method according to claim 8, wherein said pharmaceutical composition is a slow- or controlled release composition, and the administration of said extract is effected by administering to said patient one dosage unit twice daily, thereby administering two dosage units daily.

11. A method according to claim 8, wherein the administration of said extract is effected by administering to said patient from 1–50 capsules or tablets daily.

* * * * *